United States Patent [19]

Takematsu et al.

[11] 4,391,631
[45] Jul. 5, 1983

[54] HERBICIDAL COMPOSITION

[75] Inventors: Tetsuo Takematsu, Utsunomiya; Takayuki Isogawa; Yasuya Sakuraba, both of Tokyo, all of Japan

[73] Assignee: Hodogaya Chemical Co., Ltd., Tokyo, Japan

[21] Appl. No.: 306,871

[22] Filed: Sep. 29, 1981

[30] Foreign Application Priority Data

Nov. 6, 1980 [JP] Japan .................. 55-155160

[51] Int. Cl.³ .......................................... A01N 37/18
[52] U.S. Cl. .................................................. 71/118
[58] Field of Search ........................................ 71/118

[56] References Cited

U.S. PATENT DOCUMENTS

| | | | |
|---|---|---|---|
| 3,134,666 | 5/1964 | McRae | 71/118 |
| 3,154,398 | 10/1964 | McRae | 71/118 |
| 3,377,384 | 4/1968 | Dorfman | 71/124 |
| 3,382,280 | 5/1968 | Huffman | 71/118 |
| 3,443,927 | 5/1969 | Unger | 71/118 |
| 4,284,813 | 8/1981 | Takematsu et al. | 71/118 |

FOREIGN PATENT DOCUMENTS 46-28105  8/1971  Japan ..................... 71/118

Primary Examiner—Glennon H. Hollrah
Attorney, Agent, or Firm—Oblon, Fisher, Spivak, McClelland & Maier

[57] ABSTRACT

A herbicidal composition comprises a benzamide having the formula

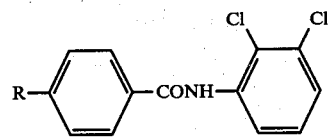

wherein R represents n—$C_4H_9O$—, $C_2H_5OCH_2O$— or n—$C_4H_9OCH_2O$— and 3,4-dichloropropionanilide as active ingredients.

3 Claims, No Drawings

HERBICIDAL COMPOSITION

BACKGROUND OF THE INVENTION

The present invention relates to a novel herbicidal composition comprising a specific benzamide and 3,4-dichloropropionanilide. The herbicidal composition of the present invention is suitable for controlling weeds at initial stage of rice plantation under various conditions.

3.4-Dichloropropionanilide has been used as a herbicide for foliage treatment of rice plant, however, the herbicidal activity is remarkably reduced in the presence of water. Therefore, when 3,4-dichloropropionanilide is used, the soil surface is exposed by a drainage of residual water and then, the herbicide is applied on the foliage (leaves and stems). The condition is kept for 2 to 3 days before flooding. The drainage and flooding operations need extra labour and various disadvantages for limitation of the time of treatment and supply of water for flooding after the treatment, are found. 3,4-Dichloropropionanilide is effective as only foliage treatment type herbicide and a herbicidal effect in a soil treatment is not substantially expected. Thus, it is necessary to apply it for 2 to 3 times at the initial stage of rice plantation. This is quite disadvantage in view of labour and economy.

The inventors have studied and dissolved the aforementioned problems.

SUMMARY OF THE INVENTION

It is an object of the present invention to provide a herbicidal composition which is effective for controlling weeds in paddy field under various conditions of cultivation such as direct sowing in well-drained paddy field or flooded field or transplantation especially at the initial growth stage.

The foregoing and other objects of the present invention have been attained by providing a herbicidal composition which comprises a benzamide having the formula

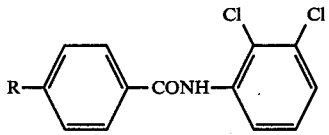

wherein R represents n—C$_4$H$_9$O—, C$_2$H$_5$OCH$_2$O— or n—C$_4$H$_9$OCH$_2$O— and 3,4-dichloropropionanilide as active ingredients.

DETAILED DESCRIPTION OF THE PREFERRED EMBODIMENTS

The herbicidal composition of the present invention comprises the active ingredients A and B. The active ingredient A is the benzamide having the formula

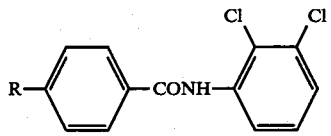

wherein R represents n—C$_4$H$_9$O—, C$_2$H$_5$OCH$_2$O— or n—C$_4$H$_9$OCH$_2$O—. The active ingredient B is 3,4-dichloropropionanilide.

The benzamides used as the active ingredient A include 4-n-butoxy-N-(2,3-dichlorophenyl)benzamide (Benzamide-(1)); 4-ethoxymethoxy-N-(2,3-dichlorophenyl)benzamide (Benzamide (2)); and 4-n-butoxymethoxy-N-(2,3-dichlorophenyl)benzamide (Benzamide (3)).

A ratio of the benzamide as the active ingredient A to 3,4-dichloropropionanilide as the active ingredient B is preferably in a range of 5 : 1 to 1 : 5, especially 3 : 1 to 1 : 3 by weight.

In the application of the herbicidal composition of the present invention, the active ingredients A and B are respectively applied at the following doses: The benzamide is applied at a rate of 50 to 1,000 g/10 are preferably 100 to 600 g/10 are especially 200 to 400 g/10 are, and 3,4-dichloropropionanilide is applied, depending upon a kind of the application, at a rate of 50 to 500 g/10 are preferably 100 to 400g/10 are especially 200 to 300 g/10 are in a foliage treatment in well-drained paddy field or non-flooded field and at a rate of 100 to 1,000 g/10 are, preferably 200 to 800 g/10 are especially 300 to 600 g/10 are in flooded filed.

The herbicidal composition of the present invention can be obtained by admixing the active ingredients A and B with a surfactant as an emulsifier and/or a dispersing agent, a liquid or solid carrier and others in the form of an emulsifiable concentrate, a wettable powder, a granule, a dust, a suspension and a paste. When water is used as a carrier, an organic solvent is used as an adjuvant.

In the form of an emulsifiable concentrate, a wettable powder, a suspension and a paste, the herbicidal composition is usually diluted with water before the application at a desired concentration, for example 10 to 10,000 ppm, preferably 100 to 5,000 ppm especially 250 to 3,000 ppm of total of the active ingredients A and B.

The liquid adjuvant is usually an organic solvent and the solid adjuvant is usually mineral fine powder. In order to impart emulsifiable property, dispersable property and spreadable property, a desired surface active ingredient is added. The active ingredient can be used by admixing with an agricultural chemical such as a fertilizer, a herbicide, an insecticide and a germicide.

In the preparation of the emulsifiable concentrate, the active ingredient is dissolved in an agricultural acceptable organic solvent and a solvent soluble emulsifier is added. Suitable solvent is not usually miscible to water and include organic solvents such as hydrocarbons, chlorinated hydrocarbons, ketones, esters, alcohols and amides. Suitable solvents include toluene, xylene, naphtha, perchloroethylene, cyclohexanone, isophorone, dimethylformamide and mixtures thereof. The optimum solvents include aromatic hydrocarbons and ketones. A mixture of solvents is usually used. The surfactants used as the emulsifier is incorporated at a ratio of 0.5 to 20 wt. % based on the emulsifiable concentrate. The surfactants can be anionic, cationic or nonionic surfactants. Suitable anoionic surfactants include higher alcholsulfates or sulfonates, alkylarylsulfonates or sulfosuccinates, such as calcium dodecylbenzenesulfonate and sodium dioclylsulfosuccinate etc. Suitable cationic surfactants include aliphatic alkylamines and aliphatic acid alkyl quaternary salts such as laurylamine hydrochloride and lauryldimethylbenzylammonium chloride. Suitable nonionic surfactants include ethylene oxide adducts of alkylphenol, aliphatic alcohol, mercaptane or aliphatic acid such as polyethyleneglycol ester of stearic acid or polyethyleneglycol ethers of palmityl alcohol or octylphenol.

The concentration of the active ingredients is in a range of 0.1 to 95 Wt. % especially 1 to 95 wt. %.

The wettable powder is prepared by incorporating the active ingredient in an inert fine powder and a surfactant. The active ingredient is usually incorporated at a ratio of 1 to 50 wt. % and the surfactant is incorporated at a ratio of 0.5 to 20 wt. %. The solid carriers usually used with the active ingredient include natural products of clay, silicates, silica, lime and carbonates and organic carriers. Suitable carriers include kaolin, jeeklite, fuller's earth talc, diatomaceous earth, magnesium lime, dolomite, and walnut shell powder.

The emulsifiers and wetting agents used in the wettable powder include polyoxyethylene-alkylphenols, aliphatic alcohols or aliphatic acids and alkylamines, alkylarylsulfonates, and dialkylsulfosuccinates. Suitable spreaders include glycerin, mannitol laurate and condensates of oleic acid and polygylcerin modified with phthalic anhydride. Suitable dispersing agents include condensates of maleic anhydride and olefine such as sodium salt of copolymer of diisobutylene and maleic acid; sodium ligninsulfonate; and sodium formaldehydenaphthalenesulfonate, etc. The dust is prepared by incorporating the active ingredient in an inert carrier used for dusts such as talc, fine clay, agalmatolite, diatomaceous earth, magnesium carbonate or wheat powder.

A concentrated dust containing the active ingredient of 10 to 80 wt. % is usually prepared. In the application as a herbicide, it is diluted with a solid carrier at a concentration of about 1 to 20 wt. %.

The granule is prepared by incorporating the active ingredient in a granular or pelletized agricultural acceptable carrier such as bentonite, kaolin clay, diatomaceous earth and talc having particle size of 8 to 60 mesh. The granule contains 1 to 50 wt. % of the active ingredient.

The amounts of the active ingredients, adjuvants and additives in the herbicidal compositions of the present invention will be further illustrated.

Emulsifiable Concentrate

Active ingredient: 0.5 to 80 wt. % preferably 5 to 40 wt. %
Surfactant: 1 to 40 wt. % preferably 5 to 20 wt. %
Liquid Carrier: 5 to 95 wt. % preferably 50 to 90 wt. %

Wettable Powder

Active ingredient: 1 to 50 wt. % preferably 5 to 30 wt. %
Surfactant: 0.5 to 20 wt. % preferably 1 to 10 wt. %
Solid carrier: 5 to 99 wt. % preferably 50 to 95 wt. %

Granule

Active ingredient: 0.5 to 50 wt. % preferably 1 to 20 wt. %
Solid carrier: 50 to 98.5 wt. % preferably 70 to 90 wt. %
Surfactant: 1 to 10 wt. % preferably 2 to 5 wt. %

Dust

Active ingredient: 0.5 to 10 wt. % preferably 1 to 5 wt. %
Solid carrier: 90 to 99.5 wt. % preferably 95 to 99 wt. %

The herbicidal composition of the present invention is effectively applicable to control weeds under various conditions of rice plant cultivation such as direct sowing in well-drained paddy field, or flooded field or transplantation at the initial growth stage. The herbicidal effect is attained regardless of water flooded and the growth of weeds can be controlled for a long time. The herbicidal composition of the present invention is remarkably effective in a foliage treatment though the composition contains the active ingredient for the soil treatment. As one of the effective applications of the herbicidal composition, the herbicidal composition can be applied in flooded water to impart the herbicidal effect beside the application in foliage treatment. The conventional herbicidal composition containing 3,4-dichloropropionanilide has been applied only in a foliage treatment. However, the herbicidal composition of the present invention can be applied not only in a foliage treatment, but also in a flooded water. This is significant in a practical application.

The herbicidal composition of the present invention can control weeds in both upland and paddy field. In the paddy field, the herbicidal composition can be applied even though it is flooded. The herbicidal effect is attained even though the herbicidal composition is put in the flooded water without direct contact with weeds.

The herbicidal compositions of the present invention will be illustrated by certain examples.

EXAMPLE 1

(Wettable Powder)

Benzamide-(1): 40 wt. parts
3,4-Dichloropropionanilide: 20 wt. parts
Kaolin clay: 35 wt. parts
Surfactant (Sorpol 5039 Toho Kagaku): 5 wt. parts These components were uniformly pulverized and mixed to prepared a wettable powder.

EXAMPLE 2

(Emulsifiable concentrate)

Benzamide-(2): 20 wt. parts
3,4-Dichloropropionanilide: 40 wt. parts
Mixture of xylene and isophorone (1:1): 30 wt. parts
Surfactant (Sorpol 800A Toho Kagaku): 10 wt. parts These components were uniformly mixed to obtain an emulsifiable concentrate.

EXAMPLE 3

(Granule)

Benzamide-(3): 7 wt. parts
3,4-Dichloropropionanilide: 17 wt. parts
Mixture of bentonite and kaolin clay (1:1): 71 wt. parts
Sodium ligninsulfonate: 5 wt. parts These components were uniformly mixed and kneaded with water and the mixture was granulated and dried to obtain a granule.

The ratios of the adjuvants can be varied in the aforementioned ranges, and the adjuvants can be selected as desired.

The herbicidal effect of the herbicidal compositions of the present invention will be illustrated by certain examples.

Test 1

Each planter having a size of 60 cm × 16.5 cm and a depth of 18 cm, was filled with an upland soil and seeds of upland rice (*Oryza sative*) (species: Akebono) were sown and the surface was covered with a soil containing seeds of weeds of large crabgrass, lambsquarters, livid amaranth and smartweed in a depth of 1 cm. In a greenhouse, they were grown. When the rice and weeds were grown at 2.5 to 3 leaf stage of rice and at 2 to 3 leaf stage of crabgrass and at 2 to 3 leaf stage of broad leaf weeds, each wettable powder was diluted with water and applied at a rate of 100 liter/10 are by spraying the diluted solution so as to contact with leaves and steams of the plants. As Reference, each composition containing only each active ingredient A or B was also used. Two and four weeks after the treatment, each phytotoxicity to rice plant and each herbicidal effect to weeds were observed. The results are shown in Table 1. The test results are shown by the following ratings.

| Herbicidal effect rating | Phytotoxicity index |
| --- | --- |
| 5: complete growth control | —: none phytotoxicity |
| 4: Growth suppression of 80-99% | ±: substantial non phytotoxicity |
| 3: Growth suppression of 60-79% | +: slight damage |
| 2: Growth suppression of 40-59% | ++: damage |
| 1: Growth suppression of 20-39% | +++: remarkable damage |
| 0: Growth suppression of less than 19% | ++++: serious damage |
|  | x: death |
| Weed: | |
| large crabgrass (*Digitaria adscendens*) | C.G. |
| lambsquarters (*Chenopodium album*) | L.S. |
| livid amaranth (*Amaranthus lividus*) | L.A. |
| smartweed (*Polygonum longisetum*) | S.W. |
| 3,4-Dichloropropionanilide: | propanil |

TABLE 1

| Dose of Active ingredient g/10a | | After two weeks | | | | |
| --- | --- | --- | --- | --- | --- | --- |
| Benzamide (1) | Propanil | Herbicidal effect | | | | Phytotoxicity |
| | | C.G. | L.S. | L.A. | S.W. | |
| 400 | — | 1 | 0 | 0 | 0 | — |
| 300 | — | 0 | 0 | 0 | 0 | — |
| 200 | — | 0 | 0 | 0 | 0 | — |
| — | 400 | 5 | 5 | 5 | 5 | — |
| — | 300 | 5 | 5 | 5 | 5 | — |
| — | 200 | 4 | 4 | 4.5 | 4.5 | — |
| 400 | 400 | 5 | 5 | 5 | 5 | — |
| 400 | 300 | 5 | 5 | 5 | 5 | — |
| 400 | 200 | 5 | 5 | 5 | 5 | — |
| 300 | 400 | 5 | 5 | 5 | 5 | — |
| 300 | 300 | 5 | 5 | 5 | 5 | — |
| 300 | 200 | 5 | 5 | 5 | 5 | — |
| 200 | 400 | 5 | 5 | 5 | 5 | — |
| 200 | 300 | 5 | 5 | 5 | 5 | — |
| 200 | 200 | 5 | 5 | 5 | 5 | — |
| 400 | — | 0 | 0 | 0 | 0 | — |
| 300 | — | 0 | 0 | 0 | 0 | — |
| 200 | — | 0 | 0 | 0 | 0 | — |
| — | 400 | 3 | 2 | 3 | 2 | — |
| — | 300 | 2 | 2 | 2 | 1 | — |
| — | 200 | 1 | 1 | 2 | 1 | — |
| 400 | 400 | 5 | 5 | 5 | 5 | — |
| 400 | 300 | 5 | 5 | 5 | 5 | — |
| 400 | 200 | 5 | 5 | 5 | 5 | — |
| 300 | 400 | 5 | 5 | 5 | 5 | — |
| 300 | 300 | 5 | 5 | 5 | 5 | — |
| 300 | 200 | 5 | 5 | 5 | 5 | — |
| 200 | 400 | 5 | 5 | 5 | 5 | — |
| 200 | 300 | 5 | 5 | 5 | 5 | — |

TABLE 1-continued

| Dose of Active ingredient g/10a | | After two weeks | | | | |
| --- | --- | --- | --- | --- | --- | --- |
| Benzamide (1) | Propanil | Herbicidal effect | | | | Phytotoxicity |
| | | C.G. | L.S. | L.A. | S.W. | |
| 200 | 200 | 5 | 5 | 5 | 5 | — |

As shown in Table 1, 3,4-dichloropropionanilide imparts excellent herbicidal effect at the early stage under the upland condition. Thus, the growth of the weeds are found after the early stage. On the other hand, the herbicidal effect of the benzamide is not substantially expected in the foliage treatment. On the contrary, the herbicidal compositions of the present invention impart excellent herbicidal effect from the application. The herbicidal effect maintained for a long time.

Test 2

In each planter having size of 60 cm × 16.5 cm and a depth of 18 cm, was filled with a paddy soil and seeds of paddy rice (species: Nihon bare) were sown and the surface was covered with a paddy soil containing seeds of weeds of barnyardgrass, monochonia, spike-flowered rotals and smallflower umbrella plant in a depth of 1 cm. Under non-flooded condition, they were grown. When the rice and weeds were grown at 3 to 3.5 leaf stage of rice and at 3.5 to 4 leaf stage of barnyardgrass (other weeds are in emergence), each emulsifiable concentrate was diluted with water and applied at a rate of 100 liter/10 are by spraying the diluted solution so as to contact with leaves and stems of the plants. As Reference, each composition containing only each active ingredient A or B was also used. Three days after the treatment, each planter was flooded in a depth of 4 cm and the condition of the depth of 4 cm was kept.

Twenty five days after the treatment, each herbicidal effect to weeds and each phytotoxicity to rice plant were observed. The results are shown in Table 2. The ratings are the same as those of Test 1.

Weed barnyardgrass (*Echinochloa crus-galli*): B.G.
monochoria (*Monochoria vaginalis*): M.C.
spike-flowered rotals (*Rotala indica koehne*): S.F.
smallflower umbrella plant (*Cyperus difformis*): S.U.

TABLE 2

| Dose of Active ingredient g/10a | | Herbicidal effect | | | | Phytotoxcity |
| --- | --- | --- | --- | --- | --- | --- |
| Benzamide (2) | Propanil | B.G. | M.C. | S.F. | S.U. | |
| 400 | — | 3 | 2 | 2 | 2 | — |
| 300 | — | 2 | 2 | 1 | 2 | — |
| 200 | — | 1 | 1 | 0 | 1 | — |
| — | 400 | 3 | 0 | 0 | 0 | — |
| — | 300 | 3 | 0 | 0 | 0 | — |
| — | 200 | 2 | 0 | 0 | 0 | — |
| 400 | 400 | 5 | 5 | 5 | 5 | — |
| 300 | 300 | 5 | 5 | 5 | 5 | — |
| 200 | 200 | 5 | 4.5 | 4 | 4.5 | — |

As shown in Table 2, the herbicidal compositions of the present invention are remarkably superior to the total herbicidal effects of each of the active ingredients A and B in the cultivation under the flooded condition after the application of the herbicidal compositions under the upland condition.

Test 3

Each planter having a size of 60 cm×16.5 cm and a depth of 18 cm, was filled with a paddy soil and the surface was covered with a soil containing seeds of weeds of barnyardgrass, monochoria, spike-flowered rotals and smallflower umbrella plant in a depth of 1 cm. After monuring (fertilizer application), flooding puddling and leveling, it was flooded in a depth of 4 cm. Eight seedlings of rice (species: Nihon bare) at 2–2.5 leaf stage (two stems for each seedling) were transplanted. In a greenhouse, they were grown. When the rice and weeds were grown at 3–3.5 leaf stage of barnyardgrass, 2–3 leaf stage of broad leaf weeds and 2–3 leaf stage of smallflower umbrella plant, each granule was uniformly poured into water. Thirty days after the treatment, each herbicidal effect to weeds and each phytotoxicity to rice plant were observed. The results are shown in Table 3. The ratings are the same as those of Test 1.

TABLE 3

| Dose of Active ingredient g/10a | | Herbicidal effect | | | | |
|---|---|---|---|---|---|---|
| Benzamide (3) | Propanil | B.G. | M.C. | S.F. | S.U. | Phytotoxicity |
| 280 | — | 3 | 0 | 0 | 0 | — |
| 210 | — | 1 | 0 | 0 | 0 | — |
| 140 | — | 0 | 0 | 0 | 0 | — |
| — | 680 | 0 | 0 | 0 | 0 | — |
| — | 510 | 0 | 0 | 0 | 0 | — |
| — | 340 | 0 | 0 | 0 | 0 | — |
| 280 | 680 | 5 | 5 | 5 | 5 | — |
| 210 | 510 | 5 | 5 | 5 | 4 | — |

TABLE 3-continued

| Dose of Active ingredient g/10a | | Herbicidal effect | | | | |
|---|---|---|---|---|---|---|
| Benzamide (3) | Propanil | B.G. | M.C. | S.F. | S.U. | Phytotoxicity |
| 140 | 340 | 4 | 3 | 3 | 2 | — |

As shown in Table 3, 3,4-dichloropropionanilide did not impart any herbicidal effect in the treatment in water, the benzamide did not impart herbicidal effect to the weeds except barnyardgrass. On the contrary, the herbicidal compositions of the present invention imparted excellent herbicidal effect to all weeds.

As shown in Tests 1, 2 and 3, the herbicidal composition of the present invention is applicable as a herbicide for rice plantation under various conditions such as cultivation of upland rice under upland condition and cultivation by transplantation under flooded condition.

We claim:

1. A herbicidal composition which consists essentially of a benzamide having the formula:

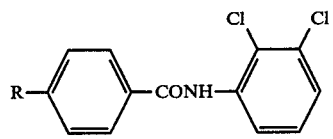

wherein R represents n—$C_4H_9O$—, $C_2H_5OCH_2O$— or n—$C_4H_9OCH_2O$— and 3,4-dichloropropionanilide as active ingredients in an effective amount for controlling weeds and an adjuvant.

2. The herbicidal composition according to claim 1 having 0.1 to 95 wt. % of the active ingredients and 99.9 to 5 wt. % of said adjuvant.

3. The herbicidal composition according to claim 1 wherein ratio of said benzamide to 3,4-dichloropropionanilide is in a range of 1:2.5 to 2:1.

* * * * *